United States Patent
Fischer et al.

(10) Patent No.: US 8,664,259 B2
(45) Date of Patent: Mar. 4, 2014

(54) OIL-BASED SUSPENSION CONCENTRATES

(75) Inventors: Reiner Fischer, Monheim (DE); Udo Reckmann, Köln (DE); Ronald Vermeer, Leverkusen (DE)

(73) Assignee: Bayer CropScience AG, Monheim (DE)

( * ) Notice: Subject to any disclaimer, the term of this patent is extended or adjusted under 35 U.S.C. 154(b) by 1584 days.

(21) Appl. No.: 10/591,128

(22) PCT Filed: Mar. 4, 2005

(86) PCT No.: PCT/EP2005/002294
§ 371 (c)(1),
(2), (4) Date: Jun. 7, 2007

(87) PCT Pub. No.: WO2005/084441
PCT Pub. Date: Sep. 15, 2005

(65) Prior Publication Data
US 2007/0276023 A1 Nov. 29, 2007

(30) Foreign Application Priority Data
Mar. 6, 2004 (DE) .......................... 10 2004 011 006

(51) Int. Cl.
A01N 43/38 (2006.01)
A61K 31/40 (2006.01)
A01N 43/36 (2006.01)

(52) U.S. Cl.
USPC ......................................... 514/409; 514/425

(58) Field of Classification Search
USPC ................................ 514/409, 425
See application file for complete search history.

(56) References Cited

U.S. PATENT DOCUMENTS

| | | | | |
|---|---|---|---|---|
| 5,705,476 A | * | 1/1998 | Hoffarth | .................. 510/535 |
| 6,140,358 A | | 10/2000 | Lieb et al. | |
| 6,255,342 B1 | | 7/2001 | Lieb et al. | |
| 6,559,156 B1 | | 5/2003 | Dimitrova | |
| 2003/0148999 A1 | | 8/2003 | Fischer et al. | |
| 2004/0157743 A1 | | 8/2004 | Rosenfeldt et al. | |
| 2007/0015825 A1 | | 1/2007 | Fischer et al. | |
| 2007/0066489 A1 | | 3/2007 | Vermeer et al. | |
| 2007/0129252 A1 | | 6/2007 | Fischer et al. | |
| 2007/0244007 A1 | | 10/2007 | Fischer et al. | |
| 2007/0254949 A1 | | 11/2007 | Bretschneider et al. | |
| 2007/0265266 A1 | | 11/2007 | Fischer et al. | |
| 2007/0270416 A1 | | 11/2007 | Funke et al. | |
| 2007/0298969 A1 | | 12/2007 | Fischer et al. | |
| 2008/0027114 A1 | | 1/2008 | Funke et al. | |
| 2008/0167188 A1 | | 7/2008 | Fischer et al. | |
| 2008/0188371 A1 | | 8/2008 | Fischer et al. | |
| 2008/0200499 A1 | | 8/2008 | Fischer et al. | |
| 2008/0220973 A1 | | 9/2008 | Fischer et al. | |
| 2008/0287435 A1 | | 11/2008 | Fischer et al. | |
| 2008/0305955 A1 | | 12/2008 | Bretschneider et al. | |
| 2008/0318776 A1 | | 12/2008 | Fischer et al. | |
| 2009/0012100 A1 | | 1/2009 | Fischer et al. | |
| 2009/0012152 A1 | | 1/2009 | Fischer et al. | |
| 2009/0029858 A1 | | 1/2009 | Fischer et al. | |
| 2009/0215624 A1 | | 8/2009 | Fischer et al. | |
| 2009/0281157 A1 | | 11/2009 | Fischer et al. | |
| 2009/0298828 A1 | | 12/2009 | Fischer et al. | |

FOREIGN PATENT DOCUMENTS

| | | | |
|---|---|---|---|
| DE | WO03/086075 | * | 4/2003 |
| WO | WO 97/36868 A1 | | 10/1997 |
| WO | WO 98/05638 A2 | | 2/1998 |
| WO | WO 98/05638 A3 | | 2/1998 |
| WO | WO 02/098230 A2 | | 12/2002 |
| WO | WO 03/000053 A1 | | 1/2003 |

OTHER PUBLICATIONS

International Search Report for International Application No. PCT/EP2005/002294, European Patent Office, Netherlands, mailed on Sep. 16, 2005.
Co-pending Application, U.S. Appl. No. 12/373,166, inventors Fischer, R., et al., filed Jul. 6, 2007.
Co-pending Application, U.S. Appl. No. 12/304,904, inventors Fischer, R., et al., filed Jun. 5, 2007.
Co-pending Application, U.S. Appl. No. 12/305,135, inventors Fischer, R., et al., filed Jun. 5, 2007.
Co-pending Application, U.S. Appl. No. 12/304,958, inventors Fischer, R., et al., filed Jun. 5, 2007.
Co-pending Application, U.S. Appl. No. 12/373,648, inventors Fischer, R., et al., filed Jul. 11, 2007.
Co-pending Application, U.S. Appl. No. 12/373,205, inventors Fischer, R., et al., filed Jul. 6, 2007.
Co-pending Application, U.S. Appl. No. 12/373,197, inventors Fischer, R., et al., filed Jul. 6, 2007.
Co-pending Application, U.S. Appl. No. 12/373,188, inventors Fischer, R., et al., filed Jul. 6, 2007.
Hull, H. M. et al., "Action of Adjuvants on Plant Surfaces," in *Adjuvants for Herbicides*, pp. 26-30, Weed Science Society of America, Illinois (1982).
Porter, M. R., *Handbook of Surfactants*, p. 34, Chapman and Hall, New York (1991).

* cited by examiner

*Primary Examiner* — Tracy Vivlemore
*Assistant Examiner* — Genevieve S Alley
(74) *Attorney, Agent, or Firm* — Sterne, Kessler, Goldstein & Fox P.L.L.C.

(57) ABSTRACT

New, oil-based suspension concentrates composed of
  at least one room-temperature-solid compound of the formula (I'),
  at least one penetrant,
  at least one vegetable oil,
  at least one nonionic surfactant and/or at least one anionic surfactant, and
  optionally one or more additives from the groups of the emulsifiers, foam inhibitors, preservatives, antioxidants, colorants and/or inert filler materials,
a process for producing these suspension concentrates, and their use for applying the active substances comprised.

8 Claims, No Drawings

OIL-BASED SUSPENSION CONCENTRATES

The present invention relates to new, oil-based suspension concentrates of cyclic keto enols, to a process for producing these formulations and to their use for applying the cyclic keto enols comprised.

Numerous water-free suspension concentrates of active agrochemical substances have already been disclosed. For instance EP-A 0 789 999 describes formulations of this type which in addition to active substance and oil comprise a mixture of different surfactants—including some which serve as penetrants—and also a hydrophobicized aluminophyllosilicate thickener. The stability of these preparations is good. A disadvantage, however, is the mandatory presence of a thickener, since it makes production more complex. Moreover, the thickener absorbs in each case some of the added amount of penetrant, which is therefore unavailable for its proper function.

From U.S. Pat. No. 6,165,940, moreover, nonaqueous suspension concentrates are already known in which besides active agrochemical substance, penetrant and surfactant or surfactant mixture there is an organic solvent, suitable solvents of this type including liquid paraffin or vegetable oil esters. The crop tolerance and/or biological activity and/or the stability of the spray liquors preparable from these formulations by dilution with water is, however, not always sufficient.

New, oil-based suspension concentrates have now been found which are composed of
at least one room-temperature-solid compound of the formula (I')

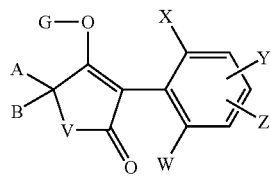

in which
V is oxygen or N-D,
X is halogen, alkyl, alkoxy, haloalkyl, haloalkoxy or cyano,
W, Y and Z independently of one another are hydrogen, halogen, alkyl, alkoxy, haloalkyl, haloalkoxy or cyano,
A is hydrogen, in each case optionally halogen-substituted alkyl, alkoxyalkyl, saturated, optionally substituted cycloalkyl, in which optionally at least one ring atom is replaced by a heteroatom,
B is hydrogen or alkyl,
A and B together with the carbon atom to which they are attached are a saturated or unsaturated, unsubstituted or substituted ring optionally including at least one heteroatom,
D is hydrogen or an optionally substituted radical from the series alkyl, alkenyl, alkoxyalkyl, saturated cycloalkyl, in which optionally one or more ring members are replaced by heteroatoms,
A and D together with the atoms to which they are attached are a saturated or unsaturated ring which optionally includes at least one heteroatom and is unsubstituted or substituted in the A,D moiety,
G is hydrogen (a) or is one of the groups

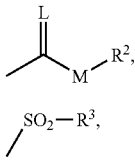

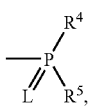

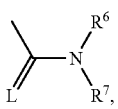

E or

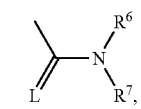

in which
E is a metal ion or an ammonium ion,
L is oxygen or sulphur,
M is oxygen or sulphur,
$R^1$ is in each case optionally halogen-substituted alkyl, alkenyl, alkoxy-alkyl, alkylthioalkyl, polyalkoxyalkyl or optionally halogen-, alkyl- or alkoxy-substituted cycloalkyl which may be interrupted by at least one heteroatom, or in each case optionally substituted phenyl, phenylalkyl, hetaryl, phenoxyalkyl or hetaryloxyalkyl,
$R^2$ is in each case optionally halogen-substituted alkyl, alkenyl, alkoxy-alkyl, polyalkoxyalkyl or is in each case optionally substituted cycloalkyl, phenyl or benzyl,
$R^3$ is optionally halogen-substituted alkyl or optionally substituted phenyl,
$R^4$ and $R^5$ independently of one another are in each case optionally halogen-substituted alkyl, alkoxy, alkylamino, dialkylamino, alkylthio, alkenyl-thio, cycloalkylthio or are in each case optionally substituted phenyl, benzyl, phenoxy or phenylthio, and
$R^6$ and $R^7$ independently of one another are hydrogen, in each case optionally halogen-substituted alkyl, cycloalkyl, alkenyl, alkoxy, alkoxyalkyl, are optionally substituted phenyl, are optionally substituted benzyl or together with the nitrogen atom to which they are attached are an optionally oxygen- or sulphur-interrupted optionally substituted ring, and
at least one penetrant,
at least one vegetable oil,
at least one nonionic surfactant and/or at least one anionic surfactant, and
optionally one or more additives from the groups of the emulsifiers, foam inhibitors, preservatives, antioxidants, colorants and/or inert filler materials.

Additionally it has been found that the oil-based suspension concentrates of the invention can be produced by mixing
at least one room-temperature-solid compound of the formula (I'),
at least one penetrant,
at least one vegetable oil,
at least one nonionic surfactant and/or at least one anionic surfactant, and optionally one or more additives from the groups of the emulsifiers, foam inhibitors, preservatives, antioxidants, colorants and/or inert filler materials with one another and optionally subsequently grinding the resultant suspension.

Finally it has been found that the oil-based suspension concentrates of the invention are highly suitable for applying the compounds of the formula (I') comprised to plants and/or their habitat.

It is to be considered extremely surprising that the oil-based suspension concentrates of the invention exhibit a much better crop tolerance despite the fact that the biological action/uptake of foreign substances in plant tissue is clearly higher in comparison to the existing formulations most similar in composition. This effect could not have been foreseen on the basis of the prior art already described.

The oil-based suspension concentrates of the invention are also notable for a series of advantages. For instance, their production is less complex than the preparation of corresponding formulations in which there are thickeners. A further advantage is that, when the concentrates of the invention are diluted with water, there is neither significant creaming nor disruptive flocculation, which is frequently the case with existing preparations of this kind. Finally, the formulations of the invention promote the crop tolerance and/or biological activity of the active components comprised, so that in comparison to conventional preparations either a higher activity is obtained or less active substance is needed.

Preference is given to oil-based oil suspension concentrates comprising compounds of the formula (I') in which the radicals have the following definition:

V is preferably oxygen or N-D,

W is preferably hydrogen, $C_1$-$C_4$-alkyl, $C_1$-$C_4$-alkoxy, chlorine, bromine or fluorine, X is preferably $C_1$-$C_4$-alkyl, $C_1$-$C_4$-alkoxy, $C_1$-$C_4$-haloalkyl, fluorine, chlorine or bromine, Y and Z are independently of one another preferably hydrogen, $C_1$-$C_4$-alkyl, halogen, $C_1$-$C_4$-alkoxy or $C_1$-$C_4$-haloalkyl, A is preferably hydrogen or in each case optionally halogen-substituted $C_1$-$C_6$-alkyl or $C_3$-$C_8$-cycloalkyl, B is preferably hydrogen, methyl or ethyl, A, B and the carbon atom to which they are attached are preferably saturated $C_3$-$C_6$-cycloalkyl, in which optionally a ring member is replaced by oxygen or sulphur, and which is optionally mono- or disubstituted by $C_1$-$C_4$-alkyl, trifluoromethyl or $C_1$-$C_4$-alkoxy, D is preferably hydrogen, in each case optionally fluorine- or chlorine-substituted $C_1$-$C_6$-alkyl, $C_3$-$C_4$-alkenyl or $C_3$-$C_6$-cycloalkyl, A and D are together preferably in each case optionally methyl-substituted $C_3$-$C_4$-alkanediyl, in which optionally a methylene group is replaced by sulphur, G is preferably hydrogen (a) or is one of the groups

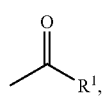
(b)

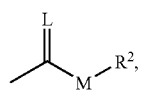
(c)

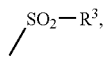
(d)

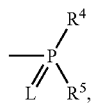
(e)

E or (f)

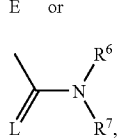
(g)

(g), particularly (a), (b), (c) or (g), in which

E is a metal ion or an ammonium ion,

L is oxygen or sulphur and

M is oxygen or sulphur, $R^1$ is preferably in each case optionally halogen-substituted $C_1$-$C_{10}$-alkyl, $C_2$-$C_{10}$-alkenyl, $C_1$-$C_4$-alkoxy-$C_1$-$C_4$-alkyl, $C_1$-$C_4$-alkylthio-$C_1$-$C_4$-alkyl or optionally fluorine-, chlorine-, $C_1$-$C_4$-alkyl- or $C_1$-$C_2$-alkoxy-substituted $C_3$-$C_6$-cycloalkyl, is optionally fluorine-, chlorine-, bromine-, cyano-, nitro-, $C_1$-$C_4$-alkyl-, $C_1$-$C_4$-alkoxy-, trifluoromethyl- or trifluoromethoxy-substituted phenyl, is in each case optionally chlorine- or methyl-substituted pyridyl or thienyl, $R^2$ is preferably in each case optionally fluorine- or chlorine-substituted $C_1$-$C_{10}$-alkyl, $C_2$-$C_{10}$-alkenyl, $C_1$-$C_4$-alkoxy-$C_2$-$C_4$-alkyl, is optionally methyl- or methoxy-substituted $C_5$-$C_6$-cycloalkyl or is in each case optionally fluorine-, chlorine-, bromine-, cyano-, nitro-, $C_1$-$C_4$-alkyl-, $C_1$-$C_4$-alkoxy-, trifluoromethyl- or trifluoromethoxy-substituted phenyl or benzyl, $R^3$ is preferably optionally fluorine-substituted $C_1$-$C_4$-alkyl or is optionally fluorine-, chlorine-, bromine-, $C_1$-$C_4$-alkyl, $C_1$-$C_4$-alkoxy, trifluoromethyl-, trifluoromethoxy-, cyano- or nitro-substituted phenyl, $R^4$ is preferably in each case optionally fluorine- or chlorine-substituted $C_1$-$C_4$-alkyl, $C_1$-$C_4$-alkoxy, $C_1$-$C_4$-alkylamino, $C_1$-$C_4$-alkylthio or is in each case optionally fluorine-, chlorine-, bromine-, nitro-, cyano-, $C_1$-$C_4$-alkoxy-, trifluoromethoxy-, $C_1$-$C_4$-alkylthio-, $C_1$-$C_4$-haloalkylthio-, $C_1$-$C_4$-alkyl- or trifluoromethyl-substituted phenyl, phenoxy or phenylthio, $R^5$ is preferably $C_1$-$C_4$-alkoxy or $C_1$-$C_4$-thioalkyl, $R^6$ is preferably $C_1$-$C_6$-alkyl, $C_3$-$C_6$-cycloalkyl, $C_1$-$C_6$-alkoxy, $C_3$-$C_6$-alkenyl, $C_1$-$C_4$-alkoxy-$C_1$-$C_4$-alkyl, $R^7$ is preferably $C_1$-$C_6$-alkyl, $C_3$-$C_6$-alkenyl or $C_1$-$C_4$-alkoxy-$C_1$-$C_4$-alkyl, $R^6$ and $R^7$ together are preferably an optionally methyl- or ethyl-substituted $C_3$-$C_6$-alkylene radical, in which optionally a carbon atom is replaced by oxygen or sulphur.

V is more preferably oxygen or N-D,

W is more preferably hydrogen, methyl, ethyl, chlorine, bromine or methoxy,

X is more preferably chlorine, bromine, methyl, ethyl, propyl, isopropyl, methoxy, ethoxy or trifluoromethyl, Y and Z are more preferably independently of one another hydrogen, fluorine, chlorine, bromine, methyl, ethyl, propyl, isopropyl, trifluoromethyl or methoxy, A is more preferably methyl, ethyl, propyl, isopropyl, butyl, isobutyl, sec-butyl, tert-butyl, cyclopropyl, cyclopentyl or cyclohexyl, B is more preferably hydrogen, methyl or ethyl, A, B and the carbon atom to which they are attached are more preferably saturated $C_6$-cycloalkyl, in which optionally a ring member is replaced by oxygen, and which is optionally monosubstituted by methyl, ethyl, trifluoromethyl, methoxy, ethoxy, propoxy or butoxy, D is more preferably hydrogen, is methyl, ethyl, propyl, isopropyl, butyl, isobutyl, allyl, cyclopropyl, cyclopentyl or cyclohexyl, A and D are together more preferably optionally methyl-substituted $C_3$-$C_4$-alkanediyl, G is more preferably hydrogen (a) or is one of the groups

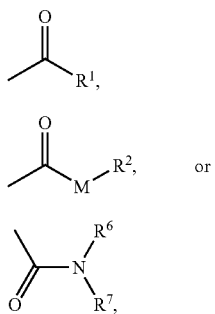

(b)

(c)

(g)

in which

M is oxygen or sulphur, $R^1$ is more preferably $C_1$-$C_8$-alkyl, $C_2$-$C_4$-alkenyl, methoxymethyl, ethoxymethyl, ethylthiomethyl, cyclopropyl, cyclopentyl or cyclohexyl, is optionally fluorine-, chlorine-, bromine-, cyano-, nitro-, methyl-, ethyl-, methoxy-, trifluoromethyl- or trifluoromethoxy-substituted phenyl, is in each case optionally chlorine- or methyl-substituted pyridyl or thienyl, $R^2$ is more preferably $C_1$-$C_8$-alkyl, $C_2$-$C_4$-alkenyl, methoxyethyl, ethoxyethyl or is phenyl or benzyl, $R^6$ and $R^7$ are independently of one another more preferably methyl, ethyl or together are a $C_5$-alkylene radical in which the $C_3$-methylene group is replaced by oxygen.

V is very preferably N-D,

W is very preferably hydrogen or methyl,

X is very preferably chlorine, bromine or methyl,

Y and Z are very preferably independently of one another hydrogen, chlorine, bromine or methyl, A, B and the carbon atom to which they are attached are very preferably saturated $C_6$-cycloalkyl, in which optionally a ring member is replaced by oxygen, and which is optionally monosubstituted by methyl, trifluoromethyl, methoxy, ethoxy, propoxy or butoxy, D is very preferably hydrogen, G is very preferably hydrogen (a) or is one of the groups (b)

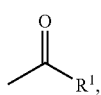

(c)

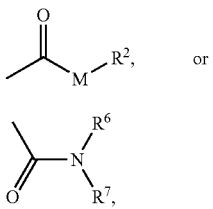

or (g)

in which

M is oxygen or sulphur, $R^1$ is very preferably $C_1$-$C_8$-alkyl, $C_2$-$C_4$-alkenyl, methoxymethyl, ethoxymethyl, ethylmethylthio, cyclopropyl, cyclopentyl, cyclohexyl or is optionally fluorine-, chlorine-, bromine-, methyl-, methoxy-, trifluoromethyl-, trifluoromethoxy-, cyano- or nitro-substituted phenyl, is in each case optionally chlorine- or methyl-substituted pyridyl or thienyl, $R^2$ is very preferably $C_1$-$C_8$-alkyl, $C_2$-$C_4$-alkenyl, methoxyethyl, ethoxyethyl, phenyl or benzyl, $R^6$ and $R^7$ are independently of one another very preferably methyl, ethyl or together are a $C_5$-alkylene radical, in which the $C_3$-methylene group is replaced by oxygen.

Particular preference is given to oil-based suspension concentrates comprising compounds of the formula (I")

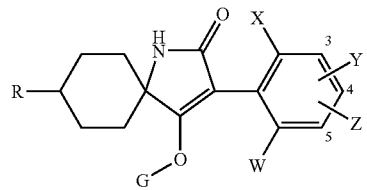

(I")

| Example No. | W | X | Y | Z | R | G | m.p. °C. |
|---|---|---|---|---|---|---|---|
| I"-1 | H | Br | 5-$CH_3$ | H | $OCH_3$ | CO-i-$C_3H_7$ | 122 |
| I"-2 | H | Br | 5-$CH_3$ | H | $OCH_3$ | $CO_2$-$C_2H_5$ | 140-142 |
| I"-3 | H | $CH_3$ | 5-$CH_3$ | H | $OCH_3$ | H | >220 |
| I"-4 | H | $CH_3$ | 5-$CH_3$ | H | $OCH_3$ | $CO_2$-$C_2H_5$ | 128 |
| I"-5 | $CH_3$ | $CH_3$ | 3-Br | H | $OCH_3$ | H | >220 |
| I"-6 | $CH_3$ | $CH_3$ | 3-Cl | H | $OCH_3$ | H | 219 |
| I"-7 | H | Br | 4-$CH_3$ | 5-$CH_3$ | $OCH_3$ | CO-i-$C_3H_7$ | 217 |
| I"-8 | H | $CH_3$ | 4-Cl | 5-$CH_3$ | $OCH_3$ | $CO_2C_2H_5$ | 162 |
| I"-9 | $CH_3$ | $CH_3$ | 3-$CH_3$ | 4-$CH_3$ | $OCH_3$ | H | >220 |
| I"-10 | $CH_3$ | $CH_3$ | 3-Br | H | $OC_2H_5$ | CO-i-$C_3H_7$ | 212-214 |
| I"-11 | H | $CH_3$ | 4-$CH_3$ | 5-$CH_3$ | $OC_2H_5$ | CO-n-$C_3H_7$ | 134 |
| I"-12 | H | $CH_3$ | 4-$CH_3$ | 5-$CH_3$ | $OC_2H_5$ | CO-i-$C_3H_7$ | 108 |
| I"-13 | H | $CH_3$ | 4-$CH_3$ | 5-$CH_3$ | $OC_2H_5$ | CO-c-$C_3H_5$ | 63 |

Suitable penetrants in the present context are all those substances which are normally used in order to improve the penetration of compounds of the formula (I') into plants. Preference is given to alkanol alkoxylates of the formula

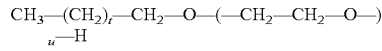

(Id)

in which t stands for numbers from 9 to 10.5 and u stands for numbers from 7 to 9.

A general definition of the alkanol alkoxylates is given by the above formula. These substances constitute mixtures of substances of the stated type with different chain lengths. For the indices, therefore, average values are calculated, which may also deviate from whole numbers.

By way of example mention may be made of alkanol alkoxylate of the formula (Id-1), in which
t stands for the average value 10.5 and
u stands for the average value 8.4.

The alkanol alkoxylates of the stated formulae are known and available commercially under the trade names: Genapol, Marlipal, Lutensol, Renex.

The compounds of the formula (I') are known:
For 3-acyl-pyrrolidine-2,4-diones pharmaceutical properties have already been described (S. Suzuki et al. Chem. Pharm. Bull. 15 1120 (1967)). Furthermore, N-phenylpyrrolidine-2,4-diones have been synthesized by R. Schmierer and H. Mildenberger (Liebigs Ann. Chem. 1985, 1095).

EP-A-0 262 399 and GB-A-2 266 888 disclose similarly structured compounds (3-aryl-pyrrolidine-2,4-diones). Known compounds include unsubstituted, bicyclic 3-arylpyrrolidine-2,4-dione derivatives (EP-A-355 599, EP-A-415 211 and JP-A-12-053 670) and also substituted monocyclic 3-aryl-pyrrolidine-2,4-dione derivatives (EP-A-377 893 and EP-A-442 077).

Also known are polycyclic 3-arylpyrrolidine-2,4-dione derivatives (EP-A-442 073) and also 1H-arylpyrrolidine-dione derivatives (EP-A-456 063, EP-A-521 334, EP-A-596 298, EP-A-613 884, EP-A-613 885, WO 94/01 997, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/16748, WO 99/24437, WO 99/43649, WO 99/48869 and WO 99/55673, WO 01/17972, WO 01/23354, WO 01/74770, WO 04/024688, WO 04/007448, WO 04/080962 and WO 04/065366).

Additionally $\Delta^3$-dihydrofuran-2-one derivatives are known (cf. DE-A-4 014 420). The synthesis of the tetronic acid derivatives used as starting compounds (such as 3-(2-methylphenyl)-4-hydroxy-5-(4-fluorophenyl)-$\Delta^3$-dihydrofuran-2-one, for example) is likewise described in DE-A-4 014 420. Similarly structured compounds are known from the publication Campbell et al., J. Chem. Soc., Perkin Trans. 1, 1985, (8) 1567-76. Moreover, 3-aryl-$\Delta^3$-dihydrofuranone derivatives are known from EP-A-528 156, EP-A-0 647 637, WO 95/26 345, WO 96/20 196, WO 96/25 395, WO 96/35 664, WO 97/01 535, WO 97/02 243, WO 97/36 868, WO 98/05638, WO 98/25928, WO 99/16748, WO 99/43649, WO 99/48869, WO 99/55673, WO 01/17 972, WO 01/23354, WO 01/74770, WO 04/024688 and WO 04/080962.

Suitable plant oils include all oils which can normally be used in agrochemical compositions and can be obtained from plants. Examples that may be mentioned include sunflower oil, rapeseed oil, corn oil, olive oil and soya-bean oil.

The oil-based suspension concentrates of the invention comprise at least one nonionic surfactant and/or at least one anionic surfactant.

Suitable nonionic surfactants include all substances of this type that can normally be used in agrochemical compositions. Preferably mention may be made of polyethylene oxide-polypropylene oxide block copolymers, polyethylene glycol ethers of linear alcohols, reaction products of fatty acids with ethylene oxide and/or propylene oxide, and also polyvinyl alcohol, polyvinylpyrrolidone, copolymers of polyvinyl alcohol and polyvinylpyrrolidone, and also copolymers of (meth) acrylic acid and (meth)acrylic esters, and also alkyl ethoxylates and alkylaryl ethoxylates, which optionally may be phosphated and optionally may be neutralized with bases, it being possible for mention to be made, by way of example, of sorbitol ethoxylates.

Suitable anionic surfactants include all substances of this type that can normally be used in agrochemical compositions. Preference is given to alkali metal salts and alkaline earth metal salts of alkylsulphonic acids or alkylarylsulphonic acids.

Suitable additives which may be included in the formulations of the invention are emulsifiers, spreaders, foam inhibitors, preservatives, antioxidants, colorants and inert filler materials. Suitable spreaders include all substances that can normally be used for this purpose in agrochemical compositions. Preference is given to alkylsiloxanes.

Preferred emulsifiers are ethoxylated nonylphenols, reaction products of alkylphenols with ethylene oxide and/or propylene oxide, ethoxylated arylalkylphenols, and also ethoxylated and propoxylated arylalkylphenols, and also sulphated or phosphated arylalkyl ethoxylates and/or arylalkyl ethoxy-propoxylates, it being possible to mention, by way of example, sorbitan derivatives, polyethylene oxide-sorbitan fatty acid esters and sorbitan fatty acid esters.

Suitable foam inhibitors include all substances that can normally be used for this purpose in agrochemical compositions. Preference is given to silicone oils and magnesium stearate.

Suitable preservatives include all substances that can normally be used for this purpose in agrochemical compositions of this type. Examples that may be mentioned include Preventol® (Bayer AG) and Proxel®.

Suitable antioxidants include all substances that can normally be used for this purpose in agrochemical compositions. Preference is given to 2,6-di-tert-butyl-4-methylphenol.

Suitable colorants include all substances that can normally be used for this purpose in agrochemical compositions. By way of example mention may be made of titanium dioxide, pigmentary carbon black, zinc oxide and blue pigments, and also Permanent Red FGR.

Suitable inert filler materials include all substances that can normally be used for this purpose in agrochemical compositions but do not function as thickeners. Preference is given to inorganic particles, such as carbonates, silicates and oxides, and also organic substances, such as urea-formaldehyde condensates. By way of example mention may be made of kaolin, rutile, silicon dioxide, so-called highly disperse silica, silica gels, and also natural and synthetic silicates, and additionally talc.

The amount of the individual components can be varied within a relatively wide range in the oil-based suspension concentrates of the invention. Thus the concentrations
  of compound of the formula (I') are generally between 5% and 30%, preferably between 10% and 25% by weight,
  of penetrant are generally between 5% and 30%, preferably between 15% and 25% by weight,
  of vegetable oil are generally between 20% and 55%, preferably between 25% and 50% by weight,
  of surfactants are generally between 2.5% and 30%, preferably between 5.0% and 25% by weight, and
  of additives are generally between 0% and 25%, preferably between 0% and 20% by weight.

The oil-based suspension concentrates of the invention are produced by mixing the components with one another in the respectively desired proportions. The order in which the constituents are combined with one another is arbitrary. Appropriately the solid components are used in a finely ground state. It is, however, also possible to subject the suspension which results after the constituents have been combined first to a coarse grinding and then to a fine grinding, so that the mean particle size is below 20 μm. Preferred suspension concentrates are those in which the solid particles have a mean size between 1 and 10 μm.

The temperatures when carrying out the process of the invention can be varied within a certain range. The work is carried out generally at temperatures between 10° C. and 60° C., preferably between 15° C. and 40° C. Equipment suitable for carrying out the process of the invention includes customary mixing and grinding apparatus which is used for producing agrochemical formulations.

The oil-based suspension concentrates of the invention constitute formulations which remain stable even following prolonged storage at elevated temperatures or in the cold, since no crystal growth is observed. By dilution with water they can be converted into homogeneous spray liquids. These spray liquids are applied by customary methods, i.e., for example, by spraying, pouring or injecting.

The application rate of the oil-based suspension concentrates of the invention can be varied within a relatively wide range. It is guided by the particular active agrochemical substances and by their amount in the formulations.

With the aid of the oil-based suspension concentrates of the invention it is possible to deliver active agrochemical substances to plants and/or their habitat in a particularly advantageous way. The active agrochemical substances included develop a better biological activity (in particular a better insecticidal action and/or better crop tolerance) than in the case of application in the form of the corresponding conventional formulations.

In accordance with the invention it is possible to treat all plants and plant parts. By plants here are meant all plants and plant populations, such as desirable and unwanted wild plants or crop plants (including naturally occurring crop plants). Crop plants may be plants which can be obtained by conventional breeding and optimization methods or by biotechnological and gene-technological methods or combinations of these methods, including the transgenic plants and including the plant cultivars which can or cannot be protected by varietal property rights. By plant parts are to be meant all above-ground and below-ground parts and organs of the plants, such as shoot, leaf, flower and root, an exemplary listing embracing leaves, needles, stems, trunks, flowers, fruit bodies, fruits and seeds and also roots, tubers and rhizomes. The plant parts also include harvested material and also vegetative and generative propagation material, examples being seedlings, tubers, rhizomes, cuttings and seeds.

The treatment of the plants and plant parts in accordance with the invention with the suspension concentrates is carried out directly or by action on their environment, habitat or storage area in accordance with the customary treatment methods, for example by dipping, spraying, squirting, evaporating, atomizing, or brush application and, in the case of propagation material, especially seeds, additionally by single or multiple coating.

As already mentioned above, all plants and their parts can be treated in accordance with the invention. In one preferred embodiment, wild plant species and plant varieties, or those obtained by conventional biological breeding methods, such as crossing or protoplast fusion, and also parts thereof, are treated. In a further preferred embodiment transgenic plants and plant varieties, which have been obtained by gene-technological methods in combination where appropriate with conventional methods (genetic modified organisms), and parts thereof, are treated. The term "parts" or "parts of plants" or "plant parts" has been elucidated above.

With particular preference, plants of the plant varieties that are in each case available commercially or in use are treated in accordance with the invention. By plant varieties are meant plants having novel properties (traits) which have been bred by conventional breeding, by mutagenesis or by recombinant DNA techniques. They may be varieties, biotypes and genotypes.

Depending on the plant species or plant varieties, their location and growth conditions (soils, climate, vegetation period, nutrition) the treatment according to the invention may also result in superadditive (synergistic) effects. Thus, for example, reduced application rates and/or extensions in the spectrum of action and/or an increase in the effect of the substances and compositions that can be used in accordance with the invention, better plant growth, increased tolerance to high or low temperatures, increased tolerance to drought or to water content or soil salt content, increased flowering performance, easier harvesting, accelerated maturation, higher harvesting yields, greater quality and/or higher nutritional value of the harvested products, higher storage capacity and/or processing capability of the harvested products are possible that go beyond the effects that were actually to be expected.

The preferred transgenic (i.e., obtained by gene technology) plants or plant varieties for treatment in accordance with the invention include all plants which by virtue of the gene-technological modification received genetic material which endows these plants with particularly advantageous, valuable traits. Examples of such traits are better plant growth, increased tolerance to high or low temperatures, increased tolerance to drought or to water content or soil salt content, increased flowering performance, easier harvesting, accelerated maturation, higher harvesting yields, greater quality and/or higher nutritional value of the harvested products, higher storage capacity and/or processing capability of the harvested products. Further and particularly emphasized examples of such traits are a heightened defense of the plants against animal and microbial pests, such as against insects, mites, phytopathogenic fungi, bacteria and/or viruses, and also increased tolerance of the plants to particular active herbicidal substances. Examples of transgenic plants include the important crop plants, such as cereals (wheat, rice), maize, soya, potatoes, cotton, oilseed rape, beet, sugar cane and also fruit plants (with the fruits apples, pears, citrus fruits and grapes), particular emphasis being given to maize, soya, potatoes, cotton and oilseed rape. Traits given particular emphasis are the heightened defense of the plants against insects, by means of toxins which form in the plants, particularly those generated in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) ("Bt plants" below). Further traits given particular emphasis are the increased defense of plants against fungi, bacteria and viruses as a result of Systemic Acquired Resistance (SAR), systemin, phytoalexins, elicitors and also resistance genes, and proteins and toxins expressed accordingly. Further traits given particular emphasis include the increased tolerance of the plants to certain active herbicidal substances, examples being imidazolinones, sulphonylureas, glyphosate or phosphinotricin (e.g. "PAT" gene). The genes which impart the desired traits in each case may also occur in combinations with one another in the transgenic plants. Examples that may be mentioned of "Bt plants" include maize varieties, cotton varieties, soya varieties and potato varieties which are sold under the trade names YIELD GARD® (e.g. maize, cotton, soya), KnockOut® (e.g. maize), StarLink® (e.g. maize), Bollgard® (cotton), Nucotn® (cotton) and NewLeaf® (potato). Examples that may be mentioned of herbicide-tolerant plants include maize varieties, cotton varieties and soya varieties which are sold under the trade names Roundup Ready® (tolerance to glyphosate, e.g. maize, cotton, soya), Liberty Link® (tolerance to phosphinotricin, e.g. oilseed rape), IMI® (tolerance to imidazolinones) and STS® (tolerance to sulphonylureas, e.g. maize). Herbicide-resistant plants (bred conventionally for herbicide tolerance) that may be mentioned also include the varieties (e.g. maize) sold under the name Clearfield®. It will be appreciated that these remarks also apply to plant varieties to be developed in the future or to appear on the market in the future and possessing these genetic traits or genetic traits developed in the future.

The plants recited can be treated with particular advantage with the suspension concentrates of the invention. The ranges of preference indicated above for the suspension concentrates also apply to the treatment of these plants. Particular emphasis may be given to the treatment of plants with the suspension concentrates recited specifically in the present text.

The invention is illustrated by the following examples.

EXAMPLES

Preparation Examples

Example I

To prepare a suspension concentrate
100.0 g of the compound of the formula (I"-4)
100.0 g of polyoxyethylene-sorbitol oleate
70.0 g of a mixture of polyalkoxylated alcohols (Atlox 4894)
30.0 g of lignin sulphonate (Borresperse NA)
0.5 g of polydimethylsiloxane
2.0 g of anhydrous citric acid
2.0 g of 2,6-di-tert-butyl-4-methylphenol
are introduced with stirring at room temperature into a mixture of
250.0 g of the compound of the formula (I-d-1) and
450.0 g of sunflower oil.

After the end of addition the mixture is stirred at room temperature for a further 10 minutes. The resultant homogeneous suspension is subjected first to coarse grinding and then to fine grinding, giving a suspension in which 90% of the particulate solids have a particle size below 6 µm.

Comparative Example I

To prepare a suspension concentrate
100 g of the compound (I"-4)
100 g of polyoxyethylene-sorbitol oleate
80 g of a mixture of polyalkoxylated alcohols (Atlox 4894)
20 g of lignin sulphonate (Borresperse NA)
0.5 g of polydimethylsiloxane
2.0 g of anhydrous citric acid
2.0 g of 2,6-di-tert-butyl-4-methylphenol
are introduced with stirring at room temperature into a mixture of
250 g of the compound RO $(EO)_8$ $(PO)_4$—H
in which
R is straight-chain or branched alkyl having 12 to 15 carbon atoms,
EO is $CH_2$—$CH_2$—O and
PO is

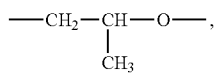

and
450.0 g of sunflower oil.

After the end of addition the mixture is stirred at room temperature for a further 10 minutes. The resultant homogeneous suspension is subjected first to coarse grinding and then to fine grinding, giving a suspension in which 90% of the particulate solids have a particle size below 6 µm.

Comparative Example II

To prepare a suspension concentrate
100 g of the compound (I"-4)
100 g of polyoxyethylene-sorbitol oleate
80 g of a mixture of polyalkoxylated alcohols (Atlox 4894)
20 g of lignin sulphonate (Borresperse NA)
0.5 g of polydimethylsiloxane
2.0 g of anhydrous citric acid
2.0 g of 2,6-di-tert-butyl-4-methylphenol
are introduced with stirring at room temperature into a mixture of
250 g of the compound $C_{13}H_{27}$—O-$(EO)_{10}$—H
in which
EO is $CH_2$—$CH_2$—O and
450.0 g of sunflower oil.

After the end of addition the mixture is stirred at room temperature for a further 10 minutes. The resultant homogeneous suspension is subjected first to coarse grinding and then to fine grinding, giving a suspension in which 90% of the particulate solids have a particle size below 6 µm.

Testing of OD Formulations for Plant Tolerance

Bean plants (*Phaseolus vulgaris*), cucumber plants (*Cucumis sativus*) and soya plants (*Glycine max*) are treated at the 1- to 2-leaf stage by spraying to runoff, the spray liquor being applied to the top face of the leaf at an active substance concentration of 400 ppm. The experiment is replicated at least twice. After the desired time the plant damage in % is measured. 100% here means that the plant has died off completely, while 0% means that the plant is undamaged in comparison to the untreated control.

Results of Glasshouse Experiments with 100-OD Formulations for Plant Tolerance.

TABLE 1

Damage to the new growth in %; 7 d after application

| | Bean | Cucumber | Soya |
| --- | --- | --- | --- |
| Example I | 0 | 5 | 0 |
| Comparative Example I | 0 | 40 | 10 |

TABLE 2

Damage to the new growth in %; 14 d after application

| | Bean | Cucumber | Soya |
| --- | --- | --- | --- |
| Example I | 0 | 0 | 0 |
| Comparative Example I | 5 | 50 | 5 |

TABLE 3

Damage to the new growth in %; 7 d after application

| | Bean | Cucumber | Soya |
|---|---|---|---|
| Example I | 0 | 5 | 0 |
| Comparative Example II | 10 | 40 | 0 |

TABLE 4

Damage to the new growth in %; 14 d after application

| | Bean | Cucumber | Soya |
|---|---|---|---|
| Example I | 0 | 0 | 0 |
| Comparative Example II | 20 | 70 | 10 |

Testing of OD Formulations for Biological Activity

Cotton and cabbage plants at the 2-leaf stage, infected respectively with *Aphis gossypii* (APHIGO) and *Myzus persicae* (MYZUPE), are treated with the active substance solution (for amounts see table). The water application rate in this case, converted, amounts to 300 l/ha. The cabbage plants are incubated under glass at 20° C. and the cotton plants at 25° C. After the desired time the activity is evaluated in comparison to the untreated control.

TABLE 5

5 d after application

| | Cotton (APHIGO) | | | Cabbage (MYZUPE) | | |
|---|---|---|---|---|---|---|
| Concentration | Example I | Comparative Example I | Comparative Example II | Example I | Comparative Example I | Comparative Example II |
| 4.8 g active substance/ha | 93 | 70 | 77 | 83 | 70 | 53 |

The invention claimed is:

1. An oil-based suspension concentrate composition comprising
at least one room-temperature-solid compound of the formula (I')

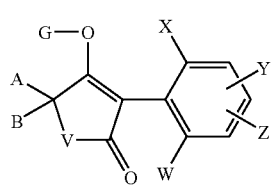

(I')

in which
V is oxygen or N-D,
X is halogen, alkyl, alkoxy, haloalkyl, haloalkoxy or cyano,
W, Y and Z independently of one another are hydrogen, halogen, alkyl, alkoxy, haloalkyl, haloalkoxy or cyano,
A is hydrogen, in each case optionally halogen-substituted alkyl, alkoxyalkyl, saturated, optionally substituted cycloalkyl, in which optionally at least one ring atom is replaced by a heteroatom,
B is hydrogen or alkyl,
A and B together with the carbon atom to which they are attached are a saturated or unsaturated, unsubstituted or substituted ring optionally including at least, one heteroatom,
D is hydrogen or an optionally substituted alkyl, alkenyl, alkoxyalkyl, or saturated cycloalkyl, in which optionally one or more ring members are replaced by heteroatoms, or
A and D together with the atoms to which they are attached are a saturated or unsaturated ring which optionally includes at least one heteroatom and is unsubstituted or substituted in the A,D moiety,
G is hydrogen (a) or is one of the groups

(b)

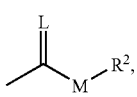
(c)

(d)

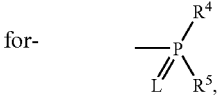
(e)

E or (f)

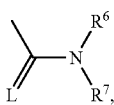
(g)

in which
E is a metal ion or an ammonium ion,
L is oxygen or sulphur,
M is, oxygen or sulphur,
$R^1$ is in each case optionally halogen-substituted alkyl, alkenyl, alkoxyalkyl, alkylthioalkyl, polyalkoxyalkyl or optionally halogen-, alkyl- or alkoxy-substituted cycloalkyl which is optionally interrupted by at least one heteroatom, or in each case optionally substituted phenyl, phenylalkyl, heteroaryl, phenoxyalkyl or hetaryloxyalkyl,
$R^2$ is in each case optionally halogen-substituted alkyl, alkenyl, alkoxyalkyl, polyalkoxyalkyl or is in each case optionally substituted cycloalkyl, phenyl or benzyl, R³ is optionally halogen-substituted alkyl or optionally substituted phenyl, R⁴ and R⁵ independently of one another are in each case optionally halogen-substituted alkyl, alkoxy, alkylamino, dialkylamino, alkylthio, alkenylthio, cycloalkylthio or are in each case optionally substituted phenyl, benzyl, phenoxy or phenylthio, and R⁶ and R⁷ independently of one another are hydrogen, in each case optionally halogen-substituted alkyl, cycloalkyl, alkenyl, alkoxy, alkoxyalkyl, are optionally substituted phenyl, are optionally substituted benzyl or together with the nitrogen atom to which they are attached are an optionally oxygen- or sulphur-interrupted optionally substituted ring, at least one penetrant that is an alkanol alkoxylate of the formula (Id)

$$CH_3-(CH_2)_t-CH_2-O-(-CH_2-CH_2-O-)_u-H \quad (Id)$$

in which
t stands for an average value from 9 to 10.5, and
u stands for an average value from 7 to 9, at least one vegetable oil,
at least one nonionic surfactant and/or at least one anionic surfactant, and optionally one or more additives selected from the group consisting of emulsifiers, foam inhibitors, preservatives, antioxidants, colorants and inert filler materials, wherein,
said compound of the formula (I') is between 5% and 30% by weight;
said penetrant is between 5% and 30% by weight,
said vegetable oil is between 20% and 55% by weight,
said surfactant is between 2.5% and 30% by weight, and
said optionally one or more additives are between 0% and 25% by weight.

2. The composition according to claim 1, in which
V is oxygen or N-D,
W is hydrogen, C₁-C₄-alkyl, C₁-C₄-alkoxy, chlorine, bromine or fluorine,
X is C₁-C₄-alkyl, C₁-C₄-alkoxy, C₁-C₄-haloalkyl, fluorine, chlorine or bromine,
Y and Z are independently of one another hydrogen, C₁-C₄-alkyl, halogen, C₁-C₄-alkoxy or C₁-C₄-haloalkyl,
A is hydrogen or in each case optionally halogen-substituted C₁-C₆-alkyl or C₃-C₈-cycloalkyl,
B is hydrogen, methyl or ethyl,
A, B and the carbon atom to which they are attached are saturated C₃-C₆-cycloalkyl, in which optionally a ring member is replaced by oxygen or sulphur, and which is optionally mono- or disubstituted by C₁-C₄-alkyl, trifluoromethyl or C₁-C₄-alkoxy,
D is hydrogen, in each case optionally fluorine- or chlorine-substituted C₁-C₆-alkyl, C₃-C₄-alkenyl or C₃-C₆-cycloalkyl,
A and D are together in each case optionally methyl-substituted C₃-C₄-alkanediyl, in which optionally a methylene group is replaced by sulphur,
G is hydrogen (a) or is one of the groups

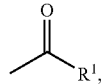
(b)

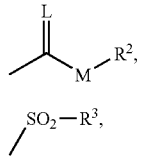
(c)

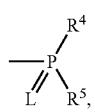
(d)

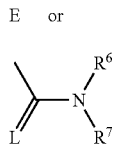
(e)

E (f)

or

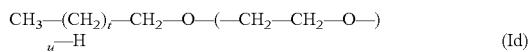
(g)

in which
B is a metal ion or an ammonium ion,
L is oxygen or sulphur,
M is oxygen or sulphur,
R¹ is in each case optionally halogen-substituted C₁-C₁₀-alkyl, C₂-C₁₀-alkenyl, C₁-C₄-alkoxy-C₁-C₄-alkyl, C₁-C₄-alkylthio-C₁-C₄-alkyl or optionally fluorine-, chlorine-, C₁-C₄-alkyl- or C₁-C₂-alkoxy-substituted C₃-C₆-cycloalkyl,
is optionally fluorine-, chlorine-, bromine-, cyano-, nitro-, C₁-C₄-alkyl-, C₁-C₄-alkoxy-, trifluoromethyl- or trifluoromethoxy-substituted phenyl,
is in each case optionally chlorine- or methyl-substituted pyridyl or thienyl,
R² is in each case optionally fluorine- or chlorine-substituted C₁-C₁₀-alkyl, C₂-C₁₀-alkenyl, or C₁-C₄-alkoxy-C₂-C₄-alkyl,
is optionally methyl- or methoxy-substituted C₅-C₆-cycloalkyl or
is in each case optionally fluorine-, chlorine-, bromine-, cyano-, nitro-, C₁-C₄-alkyl-, C₁-C₄-alkoxy-, trifluoromethyl- or trifluoromethoxy-substituted phenyl or benzyl,
R³ is optionally fluorine-substituted C₁-C₄-alkyl or is optionally fluorine-, chlorine-, bromine-, C₁-C₄-alkyl, C₁-C₄-alkoxy, trifluoromethyl-, trifluoromethoxy-, cyano- or nitro-substituted phenyl,
R⁴ is, in each case optionally fluorine- or chlorine-substituted C₁-C₄-alkyl, C₁-C₄-alkoxy, C₁-C₄-alkylamino, C₁-C₄-alkylthio or is in each case optionally fluorine-, chlorine-, bromine-, nitro-, cyano-, C₁-C₄-alkoxy-, trifluoromethoxy-, C₁-C₄-alkylthio-, C₁-C₄-haloalkylthio-, C₁-C₄-alkyl- or trifluoromethyl-substituted phenyl, phenoxy or phenylthio,
R⁵ is C₁-C₄-alkoxy or C₁-C₄-thioalkyl,
R⁶ is C₁-C₆-alkyl, C₃-C₆-cycloalkyl, C₁-C₆-alkoxy, C₃-C₆-alkenyl, or C₁-C₄-alkoxy-C₁-C₄-alkyl,
R⁷ is C₁-C₆-alkyl, C₃-C₆-alkenyl or C₁-C₄-alkoxy-C₁-C₄-alkyl,
R⁶ and R⁷ together are an optionally methyl- or ethyl-substituted C₃-C₆-alkylene radical, in which optionally a carbon atom is replaced by oxygen or sulphur.

3. The composition according to claim 1, in which
V is oxygen or N-D,
W is hydrogen, methyl, ethyl, chlorine, bromine or methoxy, X is chlorine, bromine, methyl, ethyl, propyl, isopropyl, methoxy, ethoxy or trifluoromethyl, Y and Z are independently of one another hydrogen, fluorine, chlorine, bromine, methyl, ethyl, propyl, isopropyl, trifluoromethyl or methoxy, A is methyl, ethyl, propyl, isopropyl, butyl, isobutyl, sec-butyl, tert-butyl, cyclopropyl, cyclopentyl or cyclohexyl, B is hydrogen, methyl or ethyl, A, B and the carbon atom to which they are attached are saturated $C_6$-cycloalkyl, in which optionally a ring member is replaced by oxygen, and which is optionally monosubstituted by methyl, ethyl, trifluoromethyl, methoxy, ethoxy, propoxy or butoxy, D is hydrogen, is methyl, ethyl, propyl, isopropyl, butyl, isobutyl, allyl, cyclopropyl, cyclopentyl or cyclohexyl, A and D are together optionally methyl-substituted $C_3$-$C_4$-alkanediyl, G is hydrogen (a) or is one of the groups

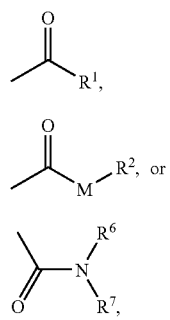

in which

M is oxygen or sulphur, $R^1$ is $C_1$-$C_8$-alkyl, $C_2$-$C_4$-alkenyl, methoxymethyl, ethoxymethyl, ethylthiomethyl, cyclopropyl, cyclopentyl or cyclohexyl,
 is optionally fluorine-, chlorine-, bromine-, cyano-, nitro-, methyl-, ethyl-, methoxy-, trifluoromethyl- or trifluoromethoxy-substituted phenyl,
 is in each case optionally chlorine- or methyl-substituted pyridyl or thienyl, $R^2$ is $C_1$-$C_8$-alkyl, $C_2$-$C_4$-alkenyl, methoxyethyl, ethoxyethyl or is phenyl or benzyl, $R^6$ and $R^7$ are independently of one another methyl, ethyl or together are a $C_5$-alkylene radical in which the $C_3$-methylene group is replaced by oxygen.

4. The composition according to claim 1, in which

V is N-D,

W is hydrogen or methyl,

X is chlorine, bromine or methyl,

Y and Z are independently of one another hydrogen, chlorine, bromine or methyl,

A, B and the carbon atom to which they are attached are saturated $C_6$-cycloalkyl, in which optionally a ring member is replaced by oxygen, and which is optionally monosubstituted by methyl, trifluoromethyl, methoxy, ethoxy, propoxy or butoxy, D is hydrogen, G is hydrogen (a) or is one of the groups

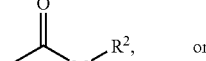

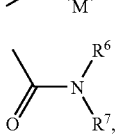

in which

M is oxygen or sulphur, $R^1$ is $C_1$-$C_8$-alkyl, $C_2$-$C_4$-alkenyl, methoxymethyl, ethoxymethyl, ethylmethylthio, cyclopropyl, cyclopentyl, or cyclohexyl or
 is optionally fluorine-, chlorine-, bromine-, methyl-, methoxy-, trifluoromethyl-, trifluoromethoxy-, cyano- or nitro-substituted phenyl,
 is in each case optionally chlorine- or methyl-substituted pyridyl or thienyl, $R^2$ is $C_1$-$C_8$-alkyl, $C_2$-$C_4$-alkenyl, methoxyethyl, ethoxyethyl, phenyl or benzyl, $R^6$ and $R^7$ are independently of one another methyl, ethyl or together are a $C_5$-alkylene radical, in which the $C_3$-methylene group is replaced by oxygen.

5. The composition according to claim 1, in which

V is N—H, and

A and B together with the carbon atom to which they are attached are a substituted six-membered ring

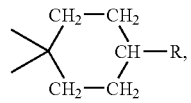

and the substituents W, X, Y, Z, G and R have the definitions indicated in the table

| W | X | Y | Z | R | G |
|---|---|---|---|---|---|
| H | Br | 5-$CH_3$ | H | $OCH_3$ | CO-i-$C_3H_7$ |
| H | Br | 5-$CH_3$ | H | $OCH_3$ | $CO_2$—$C_2H_5$ |
| H | $CH_3$ | 5-$CH_3$ | H | $OCH_3$ | H |
| H | $CH_3$ | 5-$CH_3$ | H | $OCH_3$ | $CO_2$—$C_2H_5$ |
| $CH_3$ | $CH_3$ | 3-Br | H | $OCH_3$ | H |
| $CH_3$ | $CH_3$ | 3-Cl | H | $OCH_3$ | H |
| H | Br | 4-$CH_3$ | 5-$CH_3$ | $OCH_3$ | CO-i-$C_3H_7$ |
| H | $CH_3$ | 4-Cl | 5-$CH_3$ | $OCH_3$ | $CO_2C_2H_5$ |
| $CH_3$ | $CH_3$ | 3-$CH_3$ | 4-$CH_3$ | $OCH_3$ | H |
| $CH_3$ | $CH_3$ | 3-Br | H | $OC_2H_5$ | CO-i-$C_3H_7$ |
| H | $CH_3$ | 4-$CH_3$ | 5-$CH_3$ | $OC_2H_5$ | CO-n-$C_3H_7$ |
| H | $CH_3$ | 4-$CH_3$ | 5-$CH_3$ | $OC_2H_5$ | CO-i-$C_3H_7$ |
| H | $CH_3$ | 4-$CH_3$ | 5-$CH_3$ | $OC_2H_5$ | CO-c-$C_3H_5$ |

6. A process for producing a the composition according to claim 1, comprising mixing
 at least one room-temperature-solid compound of the formula (I'),
 at least one penetrant that is an alkanol alkoxylate of the formula (Id)

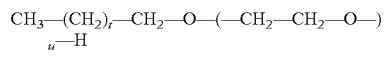

(Id)

in which
- t stands for an average value from 9 to 10.5, an
- u stands for an average value from 7 to 9, at least one vegetable oil, at least one nonionic surfactant and/or at least one anionic surfactant, and optionally one or more additives selected from the group consisting of emulsifiers, foam inhibitors, preservatives, antioxidants, colorants and/or inert filler materials, and optionally grounding the resultant suspension.

7. The composition according to claim 1, comprising said penetrant in which
- t stands for average value 10.5 and
- u stands for average value 8.4.

8. The composition according to claim 1, further comprising extenders, and/or surface-active reagents.

* * * * *